United States Patent [19]
Child et al.

[11] Patent Number: 4,880,790
[45] Date of Patent: Nov. 14, 1989

[54] (GEM-HETEROCYCLODIMETHANAMINE-N,N')PLATINUM COMPLEXES

[75] Inventors: Ralph G. Child, Pearl River; Panayota Bitha, Pomona; Joseph J. Hlavka, Tuxedo; Yang-I Lin, Nanuet, all of N.Y.

[73] Assignee: American Cyanamid Company, Stamford, Conn.

[21] Appl. No.: 824,404

[22] Filed: Jan. 31, 1986

[51] Int. Cl.$^4$ .................... A61K 31/35; C07D 309/04
[52] U.S. Cl. ....................................... 514/184; 514/99; 546/11; 548/109; 549/3; 549/206; 556/137
[58] Field of Search ...................... 549/206; 556/137; 514/99, 184

[56] References Cited

U.S. PATENT DOCUMENTS

| | | | |
|---|---|---|---|
| 4,410,544 | 10/1983 | Berg et al. | 556/137 |
| 4,500,465 | 2/1985 | Amundsen et al. | 556/137 |
| 4,730,069 | 3/1988 | Kolar et al. | 556/137 |

FOREIGN PATENT DOCUMENTS

| | | |
|---|---|---|
| 0098135 | 1/1984 | European Pat. Off. . |
| 0174542 | 3/1986 | European Pat. Off. . |
| 2340122 | 2/1974 | Fed. Rep. of Germany . |
| 2927056 | 1/1980 | Fed. Rep. of Germany . |
| 112591 | 5/1988 | Japan . |
| 2024823 | 1/1980 | United Kingdom . |
| 2128615 | 5/1984 | United Kingdom . |

OTHER PUBLICATIONS

Chemical Abstract 68:105142e.
Chemical Abstract 71:102921j.
Chemical Abstract 85:177356b.

*Primary Examiner*—Richard L. Raymond
*Attorney, Agent, or Firm*—Robert P. Raymond

[57] ABSTRACT

Organic platinum complexes active as anti-tumor agents in warm-blooded animals, and methods for synthesis of same, are described.

19 Claims, No Drawings

(GEM-HETEROCYCLODIMETHANAMINE-N,N')PLATINUM COMPLEXES

SUMMARY OF THE INVENTION

This invention is concerned with new organic compounds of the formulae:

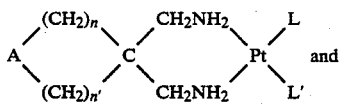
and
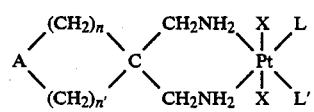

where n and n' are integers 0-3; A is selected from the group consisting of O,

N-alkyl($C_1$-$C_5$) and NCO-alkyl-($C_1$-$C_5$); L and L' are selected from the group consisting of halide, nitrate, sulfate, and a monobasic carboxylate such as acetate, hydroxy acetate and propionate; or L and L' taken together may be a dibasic carboxylate selected from the group consisting of:

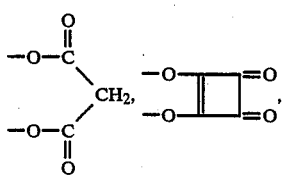

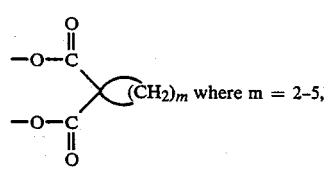, 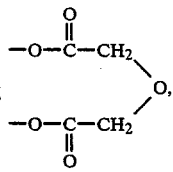

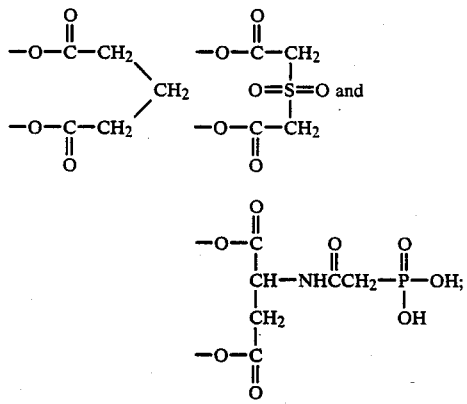

or L and L' taken together may be a tribasic carboxylate selected from the group consisting of

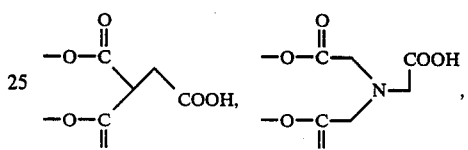

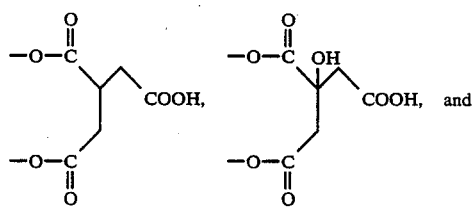

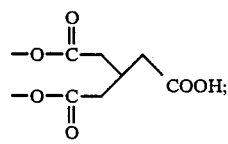

or L and L' taken together is ascorbic acid and X is selected from the group consisting of halogen and hydroxy.

The compounds of this invention may be prepared according to the following reaction schemes:

Flowchart A

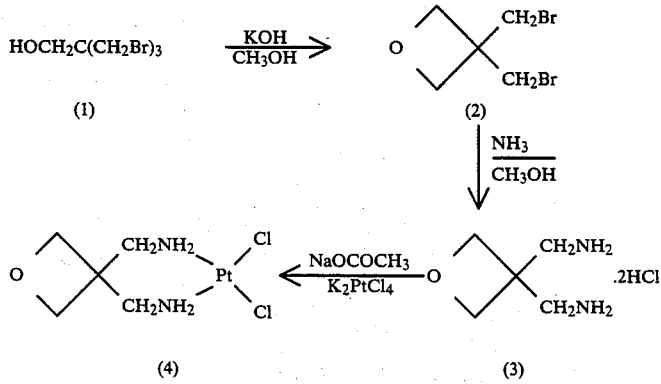

Flowchart A

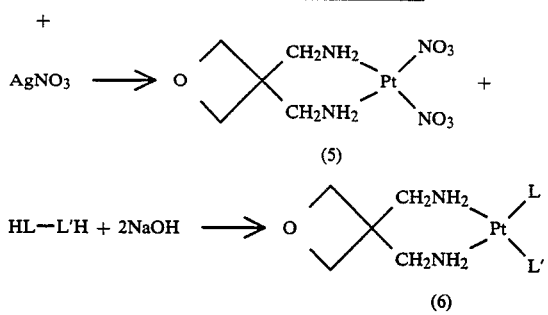

According to Flowchart A tribromopentaerythritol (1) is reacted with potassium hydroxide in methanol at reflux temperature, giving 3,3-bis(bromomethyl) oxetane (2) which is reacted with ammonia in methanol in a sealed condition, then with sodium methoxide and finally hydrochloric acid, giving 3,3-oxetanedimethanamine, dihydrochloride (3). Reaction of (3) with sodium acetate and potassium tetrachloroplatinate in water gives the product (4).

Product (4) may then be reacted with silver nitrate in water, giving the nitrate derivative (5) which is then reacted with a dibasic organic acid HL-L'H in the presence of two equivalents of sodium hydroxide giving the products (6).

Flowchart B

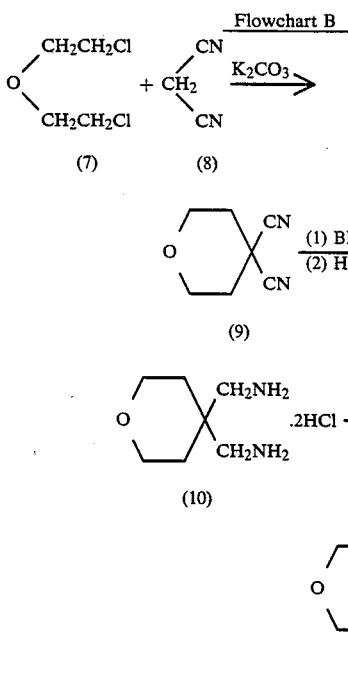

According to Flowchart B dichloroethyl ether (7) and malononitrile (8) are reacted with potassium carbonate in acetonitrile at reflux, giving tetrahydro-4H-pyran-4,4-dicarbonitrile (9) which is then reacted with 1N borane in tetrahydrofuran followed by treatment with hydrochloric acid, giving tetrahydro-4H-pyran-4,4-dimethanamine dihydrochloride (10) which is then reacted with sodium acetate and potassium tetrachloroplatinate in water, giving the product (11).

Flowchart C

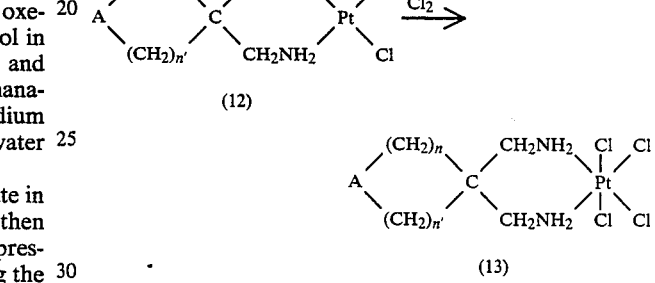

In Flowchart C, compound 13 is derived by treating 12 with chlorine gas in dilute hydrochloric acid.

Flowchart D

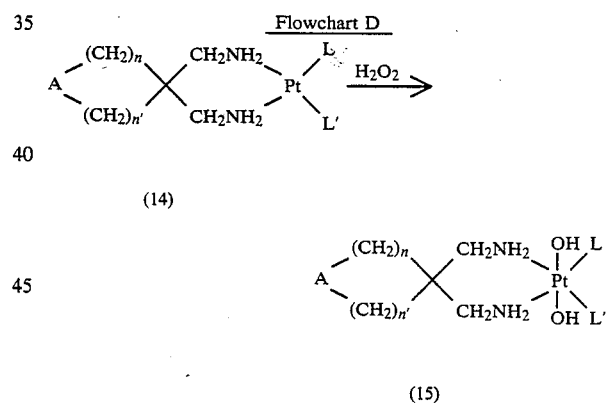

In Flowchart D, compound 15 is derived by treating 14 with hydrogen peroxide.

The novel complexed compounds of this invention possess the property of inhibiting the growth of tumors in mammals as established by the following tests.

LYMPHOCYTIC LEUKEMIA P388 TEST

The animals used were BDF/1 mice, all of one sex, weighing a minimum of 18 g and all within a 3 g weight range. There were 5 or 6 animals per test group. The tumor transplant was by intraperitoneal injection of 0.5 ml of dilute ascitic fluid containing $10^6$ cells of lymphocytic leukemia P388. The test compounds were administered intraperitoneally on days 1, 5 and 9 relative to tumor inoculation, at various doses. The animals were weighed and the survivors recorded on a regular basis for 30 days. The median survival time and the ratio of survival time for treated (T)/control (C) animals were calculated. The positive control compound was Cisplatin. The results of this test with representative compounds of this invention appear in Table I.

TABLE I

Lymphocytic Leukemia P388 Test

| Compound | Dose (mg/kg) | Median Survival (Days) | T/C × 100 (%) |
|---|---|---|---|
| dichloro(3,3-oxetanedimthanamine-N,N')platinum | 12.5 | 21 | 193 |
|  | 6.2 | 18 | 165 |
|  | 3.1 | 15 | 138 |
| Control | — | 10.9 | — |
| Cisplatin | 1 | 20.5 | 188 |
|  | 0.25 | 15 | 138 |
|  | 0.06 | 11.5 | 106 |
| (3,3-oxetanedimethanamine-N,N')[propanedioato(2-)-O$^1$,O$^3$]-platinum | 50 | 25 | 253 |
|  | 25 | 21 | 212 |
|  | 12.5 | 19 | 192 |
|  | 6.2 | 12.5 | 126 |
|  | 3.1 | 13.5 | 136 |
|  | 1.5 | 11.5 | 116 |
| Control | — | 9.9 | — |
| Cisplatin | 1 | 20 | 202 |
|  | 0.25 | 12.5 | 126 |
|  | 0.06 | 11 | 111 |
| bis(acetato-O)(3,3-oxetanedimethanamine-N,N')platinum | 12.5 | 21.5 | 217 |
|  | 6.2 | 17 | 172 |
|  | 3.1 | 11.5 | 116 |
|  | 1.5 | 11 | 111 |
| Control | — | 9.9 | — |
| Cisplatin | 1 | 20 | 202 |
|  | 0.25 | 12.5 | 126 |
|  | 0.06 | 11 | 111 |
| [1,1,2-ethanetricarboxylato(2-)-O$^1$,O$^1$](3,3-oxetanedimethanamine-N,N']platinum | 50 | 18.5 | 162 |
|  | 25 | 16 | 140 |
|  | 12.5 | 16.5 | 145 |
|  | 6.2 | 13 | 114 |
|  | 3.1 | 12.5 | 110 |
|  | 1.5 | 12 | 105 |
| Control | — | 11.4 | — |
| Cisplatin | 1 | 16 | 140 |
|  | 0.25 | 11 | 97 |
| bis(butanoato-O)(3,3-oxetanedimethanamine-N,N')platinum | 25 | 24 | 218 |
|  | 12.5 | 19 | 173 |
|  | 6.2 | 18 | 164 |
|  | 3.1 | 15 | 136 |
| Control | — | 11 | — |
| Cisplatin | 1 | 14.5 | 132 |
|  | 0.25 | 13.5 | 123 |
| [3,4-dihydroxy-3-cyclobutene-1,2-diaonato(2-)-O$^3$,O$^4$](3,3-oxetanedimethanamine-N,N')platinum | 25 | 12.5 | 114 |
|  | 12.5 | 21.5 | 195 |
|  | 6.2 | 15.5 | 141 |
|  | 3.1 | 13 | 118 |
| Control | — | 11 | — |
| Cisplatin | 1 | 14.5 | 132 |
|  | 0.25 | 13.5 | 123 |
| [1,1-cyclobutanedicarboxylato-(2-)-O$^1$,O$^1$](3,3-oxetanedimethanamine-N,N')platinum | 50 | 24 | 218 |
|  | 25 | 20 | 182 |
|  | 12.5 | 16.5 | 150 |
|  | 6.2 | 11.5 | 105 |
|  | 3.1 | 12 | 109 |
| Control | — | 11 | — |
| Cisplatin | 1 | 14.5 | 132 |
|  | 0.25 | 13.5 | 123 |
| (3,3-oxethanedimethanamine-N,N')-[[2,2'-oxybis[acetato]](2-)-O$^1$,O$^1$]platinum | 12.5 | 20.5 | 186 |
|  | 6.2 | 12.5 | 114 |
|  | 3.1 | 13 | 118 |
| Control | — | 11 | — |
| Cisplatin | 1 | 14.5 | 132 |
|  | 0.25 | 13.5 | 123 |
| (3,3-oxetanedimethanamine-N,N',)[propanedioato(2-)-O$^1$,O$^3$]-platinum | 100 | 17 | 155 |
|  | 50 | 21.5 | 195 |
|  | 25 | 14.5 | 132 |
|  | 12.5 | 14 | 127 |
|  | 6.2 | 12 | 109 |
|  | 3.1 | 12 | 109 |
| Control | — | 11 | — |
| Cisplatin | 1 | 14.5 | 132 |
|  | 0.25 | 13.5 | 123 |
| (3,3-oxetanedimethanamine-N,N',)[pentanedioato(2-)-O$^1$,O$^5$]- | 100 | 10.5 | 105 |
|  | 50 | 18.5 | 185 |

TABLE I-continued

Lymphocytic Leukemia P388 Test

| Compound | Dose (mg/kg) | Median Survival (Days) | T/C × 100 (%) |
|---|---|---|---|
| platinum | 25 | 16 | 160 |
|  | 12.5 | 14 | 140 |
|  | 6.2 | 13 | 130 |
|  | 3.1 | 12 | 120 |
| Control | — | 10 | — |
| Cisplatin | 1.25 | 25.5 | 255 |
|  | 0.62 | 20.5 | 205 |

MELANOTIC MELANOMA B16

The animals used were C57BC/6 mice, all of the same sex, weighing a minimum of 17 g and all within a 3 g weight range. There were 10 animals per test group. A 1 g portion of melanotic melanoma B$_{16}$ tumor was homogenized in 10 ml of cold balanced salt solution and a 0.5 ml aliquot of the homogenate was implanted intraperitoneally into each of the test mice. The test compounds were administered intraperitoneally on days 1 through 9, relative to tumor inoculation, at various doses. The animals were weighed and survivors recorded on a regular basis for 60 days. The median survival time for treated (T)/control (C) animals were calculated. The positive control compound was Cisplatin. The results of this test appear in Table II.

TABLE II

Melanotic Melanoma B16 Test

| Compound | Dose (mg/kg) | Median Survival (Days) | T/C × 100 (%) |
|---|---|---|---|
| (3,3-oxetanedimethanamine-N,N')[propanedioato(2-)-O$^1$,O$^3$]-platinum | 25 | 30 | 176 |
|  | 12 | 30 | 176 |
|  | 6 | 27.5 | 162 |
| Control | — | 17 | — |
| Cisplatin | 0.5 | 22.5 | 132 |
|  | 0.25 | 25 | 147 |
| bis(acetato-O)(3,3-oxetanedimethanamine-N,N')platinum | 3 | 23 | 135 |
|  | 1.5 | 19 | 112 |
|  | 0.8 | 24.5 | 144 |
| Control | — | 17 | — |
| Cisplatin | 0.5 | 22.5 | 132 |
|  | 0.25 | 25 | 147 |
| bis(butanoato-O)(3,3-oxetanedimethanamine-N,N')platinum | 3 | 26 | 153 |
| Control | — | 17 | — |
| Cisplatin | 0.5 | 22.5 | 132 |
|  | 0.25 | 25 | 147 |
| [1,1-cyclobutanedicarboxylato-(2-)-O$^1$,O$^1$](3,3-oxethanedimethanamine-N,N')platinum | 12 | 20.5 | 121 |
|  | 6 | 26 | 153 |
|  | 3 | 20 | 118 |
|  | 1.5 | 20.5 | 121 |
| Control | — | 17 | — |
| Cisplatin | 0.5 | 22.5 | 132 |
|  | 0.25 | 25 | 147 |
| dichlorc(3,3-oxetanedimethanamine-N,N')platinum | 1.5 | 26 | 137 |
|  | 0.8 | 21.5 | 113 |
| Control | — | 19 | — |
| Cisplatin | 0.4 | 29.5 | 155 |
|  | 0.2 | 25.5 | 134 |
|  | 0.1 | 20.5 | 108 |

COLON 26 ADENOCARCINOMA TEST

The animals used were Balb/C mice all of one sex, weighing a minimum of 17 g and all within a 3 g weight range. There were 5 or 6 mice per test group with three groups of 5 or 6 animals used as untreated controls for each test. The tumor implant was by intraperitoneal (or subcutaneous) injection of 0.5 ml of a 2% Colon 26 tumor brei in Eagle's MEM medium containing antibiotics. The test compounds were administered intraperitoneally on days 1, 5 and 9 (relative to tumor implant doses). The mice were weighed and deaths recorded on a regular basis for 30 days. The median survival times and the ratio of survival time for treated (T)/control (C) animals were calculated. The positive control compound was Cisplatin. The results of this test on representative compounds of this invention appear in Table III.

TABLE III
Colon 26 Adenocarcinoma Test

| Compound | Dose (mg/kg) | Median Survival (Days) | T/C × 100 (%) |
|---|---|---|---|
| (3,3-oxethanedimethanamine-N,N')- [propanedioato(2-)O$^1$,O$^3$]platinum | 50 | 27.5 | 172 |
|  | 25 | 30 | 188 |
|  | 12 | 26 | 163 |
|  | 6 | 21 | 131 |
| Control | — | 16 | — |
| Cisplatin | 1 | 25 | 156 |
|  | 0.5 | 18 | 113 |
|  | 0.25 | 18 | 113 |
| bis(acetato-O)(3,3-oxetanedimethanamine-N,N')platinum | 12 | 19.5 | 118 |
|  | 6 | 22.5 | 136 |
|  | 3 | 19 | 115 |
|  | 1.5 | 17.5 | 106 |
| Control | — | 16.5 | — |
| Cisplatin | 1 | 23 | 139 |
|  | 0.5 | 15.5 | 94 |
|  | 0.25 | 17 | 103 |
| bis(butanoato-O)(3,3-oxetane dimethanamine-N,N')platinum | 12 | 22 | 157 |
|  | 6 | 18.5 | 132 |
|  | 3 | 15.5 | 111 |
| Control | — | 14 | — |
| Cisplatin | 1 | 16.5 | 118 |
|  | 0.5 | 20.5 | 146 |
|  | 0.25 | 24 | 171 |
|  | 0.125 | 17 | 121 |
| [3,4-dihydroxy-3-cyclobutene-1,2-dionato(2-)-O$^3$,O$^4$](3,3-oxetanedimethanamine-N,N')-platinum | 3 | 16 | 114 |
| Control | — | 14 | — |
| Cisplatin | 1 | 16.5 | 118 |
|  | 0.5 | 20.5 | 146 |
|  | 0.25 | 24 | 171 |
|  | 0.125 | 17 | 121 |
| [1,1-cyclobutanedicarboxylato-(2-)-O$^1$,O$^1$](3,3-oxetanedimethanamine-N,N')platinum | 50 | 20 | 143 |
|  | 25 | 21 | 150 |
|  | 12 | 20.5 | 146 |
|  | 6 | 19 | 136 |
| Control | — | 14 | — |
| Cisplatin | 1 | 16.5 | 118 |
|  | 0.5 | 20.5 | 146 |
|  | 0.25 | 24 | 171 |
|  | 0.125 | 17 | 121 |

LYMPHOCYTIC LEUKEMIA L1210 TEST

The animals used BDF$_1$ of CD$_2$F$_1$ mice, all of one sex, weighing a minimum of 17 g and all within a 3 g weight range. There were 6 mice in each test group and 18 in control groups. The tumor transplant was by intraperitoneal injection of 0.5 ml of lymphocytic leukemia L1210 at a concentration of 10$^5$ cells per mouse. The test compounds were administered on days, 1, 5 and 9 (relative to tumor inoculaion) at various doses. The mice were weighed and survivors recorded on a regular basis for 30 days. The median survival time and the ratio of survival time for treated (T)/control (C) animals were calculated. The positive control compound was Cisplatin given intraperitoneally at the indicated doses.

The results of this test on representative compounds of this invention appear in Table IV.

TABLE IV
Lymphocytic Leukemia L1210 Test

| Compound | Dose (mg/kg) | Median Survival (Days) | T/C × 100 (%) |
|---|---|---|---|
| dichloro(3,3-oxetanedimethanamine-N,N')platinum | 6.2 | 10 | 111 |
|  | 3.1 | 12.5 | 139 |
| Control | — | 9 | — |
| Cisplatin | 2.5 | 14 | 156 |
|  | 1.25 | 12.5 | 139 |
| (3,3-oxetanedimethanamine-N,N')[propanedioato(2-)-O$^1$,O$^3$]-platinum | 50 | 13.5 | 150 |
|  | 25 | 10.5 | 117 |
|  | 12.5 | 9.5 | 106 |
| Control | — | 9 | — |
|  | 5 | 19 | 211 |
|  | 2.5 | 13.5 | 150 |
|  | 1.25 | 10 | 111 |
| bis(acetato-O)(3,3-oxetanedimethanamine-N,N')platinum | 12.5 | 13 | 144 |
|  | 6.2 | 11 | 122 |
|  | 3.1 | 9.5 | 106 |
| Control | — | 9 | — |
| Cisplatin | 5 | 19 | 211 |
|  | 2.5 | 13.5 | 150 |
|  | 1.25 | 10 | 111 |
| bis(butanoato-O)(3,3-oxetanedimethanamine-N,N')platinum | 25 | 14.5 | 161 |
|  | 12.5 | 12.5 | 139 |
|  | 6.2 | 9.5 | 106 |
| Control | — | 9 | — |
| Cisplatin | 5 | 16 | 178 |
|  | 2.5 | 12.5 | 139 |
|  | 1.25 | 10 | 111 |
| [3,4-dihydroxy-3-cyclobutene-1,2-dionato(2-)-O$^3$,O$^4$](3,3-oxetanedimethanamine-N,N')platinum | 25 | 10.5 | 117 |
|  | 12.5 | 13 | 144 |
|  | 6.2 | 9.5 | 106 |
|  | 3.1 | 9.5 | 106 |
| Control | — | 9 | — |
| Cisplatin | 5 | 16 | 178 |
|  | 2.5 | 12.5 | 139 |
|  | 1.25 | 10 | 111 |
| [1,1-cyclobutanedicarboxylato-(2-)-O$^1$,O$^1$](3,3-oxetanedimethanamine-N,N')platinum | 50 | 14 | 156 |
|  | 25 | 13 | 144 |
|  | 12.5 | 10 | 111 |
| Control | — | 9 | — |
| Cisplatin | 5 | 16 | 178 |
|  | 2.5 | 12.5 | 139 |
|  | 1.25 | 10 | 111 |

M5076 SARCOMA

The M5076 reticular cell Sarcoma is propagated as subcutaneous implants in C57B2/6 female mice. In the assays for antitumor activity, BDF$_1$ mice of either sex were inoculated intraperitoneally (ip) with 0.5 ml of a 10% tumor brei. Test compounds were administered ip on days 1, 5, 9, 13 and 17 relative to tumor inoculation on day zero. The median survival time in days was determined for each drug dose used on day 60 and the ratio of survival time for treated (T)/control (C) animals were calculated.

The results of this test on representative compounds of this invention appear in Table V, compared to the results obtained with Cisplatin.

TABLE V
M5076 Sarcoma Test

| Compound | Dose (mg/kg) | Median Survival (Days) | T/C × 100 (%) |
|---|---|---|---|
| (3,3-oxetanedimethanamine-N,N')[propanedioato(2-)-O$^1$,O$^3$]-platinum | 25 | >60 | >240 |
|  | 12 | 51.5 | 204 |
|  | 6 | 55.5 | 222 |
|  | 3 | 44.5 | 178 |
| Control | — | 25 | — |
| Cisplatin | 0.8 | >60 | >240 |

TABLE V-continued

M5076 Sarcoma Test

| Compound | Dose (mg/kg) | Median Survival (Days) | T/C × 100 (%) |
|---|---|---|---|
| bis(acetato-O)(3,3-oxetane dimethamine-N,N')platinum | 6 | >60 | >240 |
|  | 3 | 59.5 | 238 |
|  | 1.5 | 50 | 200 |
|  | 0.8 | 44.5 | 178 |
| Control | — | 25 | — |
| Cisplatin | 0.8 | >60 | >240 |
| bis(butanoato-O)(3,3-oxetane- dimethanamine-N,N')platinum | 12 | 45 | 180 |
|  | 6 | 37.5 | 150 |
|  | 3 | 37.5 | 150 |
|  | 1.5 | 35 | 140 |
| Control | — | 25 | — |
| Cisplatin | 0.8 | >60 | >240 |
| [3,4-dihydroxy-3-cyclobutene- 1,2-dionato(2-)-O$^3$,O$^4$](3,3-oxe- tanedimethanamine-N,N') platinum | 6 | 43 | 172 |
|  | 3 | 36 | 144 |
|  | 1.5 | 35 | 140 |
|  | 0.8 | 34.5 | 138 |
| Control | — | 25 | — |
| Cisplatin | 1.6 | >60 | >240 |
|  | 0.8 | 31.5 | 126 |
| [1,1-cyclobutanedicarboxylato- (2-)-O$^1$,O$^1$](3,3-oxetanedi- methanamine-N,N')platinum | 25 | >60 | >240 |
|  | 12 | 55 | 220 |
|  | 6 | 54 | 216 |
|  | 3 | 41.5 | 166 |
| Control | — | 25 | — |
| Cisplatin | 1.6 | >60 | >240 |
|  | 0.8 | 31.5 | 126 |

The invention includes novel compositions of matter and the method of inducing the regression and/or palliation of leukemia and related cancers in mammals using the novel compounds of this invention when administered in amounts ranging from about 1 mg to about 1.2 g per square meter of body surface area per day. The interrelationship of dosages for animals of various sizes and species and humans (based on mg/m$^2$ of surface area) is described by Freireich, E. J., et al., Quantitative Comparison of Toxicity of Anticancer Agents in Mouse, Rat, Hamster, Dog, Monkey and Man. Cancer Chemother. Rep., 50, No. 4, 219–244, May 1966. A preferred dosage regimen for optimum results would be from about 3 mg/m$^2$/day to about 200 mg/m$^2$/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular or subcutaneous routes.

The active compounds may be administered parenterally. Solutions or dispersions of the active compound can be prepared in water, suitably mixed with a surfactant such as hydroxypropylcellulose. Dispersions can also be prepared in glycerol, liquid polyethylene glycols, and mixtures thereof in oils. Under ordinary conditions of storage and use these preparations contains a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, liquid polyethylene glycol), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents for example, sugars or sodium chloride. Prolonged absorption of the injectable compositions can be obtained by the use in the compositions of agents which delay absorption, for example, aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subject to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is imparied as herein disclosed in detail.

The principal active ingredient is compounded for convenient and effective administration in effective amounts with a suitable, pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single, intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is sufficient amount to aid regression and palliation of the leukemia or the like, in the absence of excessive deleterious side effects of a cytotoxic nature to the host harboring the cancer. As used herein, cancer disease means blood malignancies such as leukemia, as well as other solid and non-solid malignancies such as the melanocarcinomas, lung carcinomas and mammary tumors. By regression and palliation is meant arresting or retarding the growth of the tumor or other manifestation of the disease compared to the course of the disease in the absence of treatment.

This invention will be described in greater detail in conjunction with the following, non-limiting specific examples.

EXAMPLE 1

Dichloro(3,3-oxetanedimethanamine-N,N')platinum

A mixture 162 g of tribromo pentaerythritol, 28.6 g of potassium hydroxide and 910 ml of methanol was heated at reflux for 6 hours, then filtered. The filtrate was evaporated to dryness and the residue triturated with ether, then filtered. The filtrate was vacuum distilled, giving 62.88 g of 3,3-bis(bromomethyl)oxetane (70°–73° C., 1.0–1.5 mm).

A 9.76 g portion of 3,3-bis(bromomethyl)oxetane in 30 ml of methanol was cooled in an ice bath and 13 g of dry ammonia absorbed. The reaction was sealed and the mixture stirred at room temperature for 40 hours, then evaporated to dryness. A 2.60 g portion of this residue was slurried in 10 ml of methanol and treated with a solution of 1.08 g of sodium methoxide in 15 ml of methanol. This mixture was cooled in an ice bath, stirred for 15 minutes, then evaporated to dryness. The residue was triturated with isopropanol and filtered. The filtrate was treated with 20 ml of 6N hydrochloric acid in isopropanol, stirred for ½ hour and the solid collected washed with isopropanol and dried, giving 1.32 g of 3,3-oxetanedimethanamine, dihydrochloride, mp 236° C. (dec.).

A 945 mg portion of 3,3-oxetanedimethanamine dihydrochloride in 40 ml of water was treated with 820 mg of sodium acetate and 2.075 g of potassium tetrachloroplatinate. This mixture was stirred for 3 hours, then filtered. The filtrate was allowed to stand overnight, then the resulting solid was collected, giving 440 mg of the desired product as yellow crystals, mp 270°–273° C.

EXAMPLE 2

[1,1,2-Ethanetricarboxylato(2-)-$O^1,O^1$](3,3-oxetanedimethanamine-N,N')platinum A 764 mg portion of dichloro(3,3-oxetanedimethanamine-N,N')platinum in 5 ml of water was treated with a solution of 612 mg of silver nitrate in 5 ml of water. This solution was stirred for ½ hour, then filtered and the filtrate treated with a solution of 324 mg of diglycolic acid, 4 ml of 1N sodium hydroxide and 5 ml of water. This mixture was stirred for 2 days and then filtered. The filtrate was refrigerated for 7 days. The resulting solid was collected, washed with methanol and dried, giving 50 mg of the desired product, mp 275°–280° C.

EXAMPLE 3

Bis(butanoato-O)(3,3-oxetanedimethanamine-N,N')platinum

A 764 mg portion of dichloro(3,3-oxetanedimethanamine-N,N')platinum in 5 ml of water was treated with a solution of 680 mg of silver nitrate in 5 ml of water. This solution was stirred for ½ hour, then filtered and the filtrated treated with 352 mg of butanoic acid in 4 ml of 1N sodium hydroxide and 5 ml of water. This mixture was stirred, then allowed to stand overnight and then filtered. The filtrate was concentrated to dryness, then triturated in water and dried, giving 300 mg of the desired product, mp 205°–210° C. (dec.).

EXAMPLE 4

[3,4-Dihydroxy-3-cyclobutene-1,2-dionato(2-)-$O^3,O^4$](3,3-oxetanedimethanamine-N,N')platinum A 764 mg portion of dichloro(3,3-oxetanedimethanamine-N,N')platinum was reacted with 680 mg of silver nitrate as described in Example 2. The filtrate was treated with a solution of 228 mg of 3,4-dihydroxy-3cyclobutene-1,2-dicarboxylic acid in 4 ml of 1N sodium hydroxide and 5 ml of water. The reaction was allowed to stand for 2 hours, then the solid was collected, washed with water and dried, giving 100 mg of the desired product as a yellow solid, mp 275°–280° C. (dec.).

EXAMPLE 5

[1,1-Cyclobutanedicarboxylato(2-)-$O^1,O^1$](3,3-oxetanedimethanamine-N,N')platinum A suspension of 760 mg of dichloro(3,3-oxetanedimethanamine-N,N')platinum and 716 mg of the disilver salt of 1,1-cyclobutanedicarboxylic acid in 50 ml of water was stirred in the dark for 64 hours, then filtered. The filtrate was concentrated to dryness, giving 780 mg of the desired product, mp 280°–290° C. (dec.).

EXAMPLE 6

(3,3-Oxetanedimethanamine-N,N')[[2,2'-oxybis-[acetato]](2-)-$O^1,O^1$]platinum

A mixture of 764 mg of dichloro(3,3-oxetanedimethanamine-N,N')platinum and 696 mg of the disilver salt of diglycolic acid in 50 ml of water was stirred in the dark overnight and then filtered. The filtrate was evaporated to dryness, giving 880 mg of the desired product as a colorless glass, mp 225°–228° C.

EXAMPLE 7

(3,3-Oxetanedimethanamine-N,N')[propanedioato(2-)-$O^1,O^3$]platinum, heptahydrate A mixture of 764 mg of dichloro(3,3-oxetanedimethanamine-N,N')platinum and 680 mg of silver nitrate in water was stirred for ½ hour and then filtered. The filtrate was treated with 208 mg of malonic acid and 4 ml of 1N sodium hydroxide. This mixture was allowed to stand for 3 days and the resulting crystals collected, giving 700 mg of the desired product, mp 275°–285° C. (dec.).

EXAMPLE 8

(3,3-Oxetanedimethanamine-N,N')[propanedioato(2-)-O$^1$,O$^3$]platinum, dihydrate The procedure of Example 7 was repeated. The crystalline product was recrystallized from 10 ml of water, giving 360 mg of the desired product, mp 275°–280° C. (dec.).

EXAMPLE 9

(3,3-Oxetanedimethanamine-N,N')[pentanedioato(2-)-O$^1$,O$^5$]platinum

A mixture of 382 mg of dichloro(3,3-oxetanedimethanamine-N,N')platinum and 345 mg of glutaric acid in 30 ml of water was stirred in the dark overnight and then filtered. The filtrate was evaporated to dryness, giving 410 mg of the desired product as a colorless solid, mp 220°–222° C. (dec.).

EXAMPLE 10

Bis(acetato-O)(3,3-oxetanedimethanamine-N,N')platinum

A mixture of 764 mg of dichloro(3,3-oxetanedimethanamineN,N')platinum and 668 mg of silver acetate in 50 ml of water was stirred for 2 days and then filtered. The filtrate was concentrated to dryness, giving 800 mg of the desired product as a pale yellow solid, mp >200° C.

EXAMPLE 11

(3,3-Oxetanedimethanamine-N,N')[[2,2-sulfonylbis[acetato]](2-)-O$^1$,O$^1$]platinum A 1.14 g portion of dichloro(3,3-oxetanedimethanamine-N,N')platinum was suspended in 75 ml of water and treated with 1.18 g of sulfonyldiacetic acid disilver salt. The mixture was stirred for 4 hours at room temperature and then filtered. The filtrate was concentrated to about 50 ml, allowed to stand 48 hours and the resulting said collected, giving 470 mg of the desired product as a pale purple solid with no defined melting point below 300° C.

EXAMPLE 12

Dichloro(tetrahydro-4H-pyran-4,4-dimethanamine-N,N')platinum

A mixture of 28.6 g of dichloroethyl ether, 13.2 g of malononitrile, 55.28 g of potassium carbonate and 800 ml of acetonitrile was refluxed on a steam bath for 24 hours, then filtered while hot. The filtrate was evaporated and the residue crystallized with charcoal treatment from 100 ml of ethanol, giving 9.5 g of tetrahydro-4H-pyran-4,4-dicarbonitrile as colorless plates, mp 110°–112° C.

A 180 ml portion of 1N borane in tetrahydrofuran was added rapidly, but dropwise, to a solution of 8.18 g of tetrahydro-4H-pyran-4,4-dicarbonitrile in 150 ml of tetrahydrofuran. This mixture was warmed, then cooled to room temperature in an ice bath and then stirred for 64 hours at room temperature. A 100 ml portion of ethanol was added dropwise, then the mixture was stirred for 4 hours and evaporated to dryness. The residue was taken up in 100 ml of water, acidified with 50 ml of 6N hydrochloric acid and extracted three times with ether. The remaining aqueous layer was evaporated to dryness. The residue was boiled in 300 ml of methanol and filtered while hot. The filtrate was treated with 200 ml of ether and cooled. The resulting solid was collected, washed with ether and dried, giving 8.31 g of tetrahydro-4H-pyran-4,4-dimethanamine, dihydrochloride, mp 258°–262° C. (dec.).

A mixture of 2.17 g of the above compound and 1.64 g of sodium acetate in 50 ml of water was treated with 4.15 g of potassium tetrachloroplatinate. The reaction was repeatedly filtered to remove succesive crops of black to red crystals. When no more precipitates formed the mixture was allowed to stand overnight. The gold crystals were collected, giving 400 mg of the desired product, mp 280°–282° C. (dec.).

EXAMPLE 13

[1,1-Cyclobutanedicarboxylato(2-)-O$^1$,O$^1$]tetrahydro-4H-pyran-4,4-dimethanamine-N,N') platinum A mixture of 0.82 g of dichloro(tetrahydro-4H-pyran-4,4-dimethanamine-N,N')platinum and 0.716 g of the disilver salt of 1,1-cyclobutanedicarboxylic acid in 75 ml of water was stirred in the dark overnight and then filtered and washed with water. The combined filtrate and wash was evaporated to dryness, giving 0.72 g of the desired product, mp 290°–295° C. (dec.).

EXAMPLE 14

[[2,2'-oxybis[acetato]](2-)-O$^1$,O$^1$](tetrahydro-4H-pyran-4,4-dimethanamine-N,N')platinum The procedure of Example 13 was repeated, using 0.7 g of the disilver salt of 2,2'-oxybisacetic acid in place of the disilver salt of 1,1-cyclobutanedicarboxylic acid, giving 1.0 g of the desired product, mp 218°–220° C. (dec.).

EXAMPLE 15

[Propanedioato(2-)-O$^1$,O$^3$](tetrahydro-4H-pyran-(4,4-dimethanamine-N,N')platinum The procedure of Example 13 was repeated, using 0.64 g of the disilver salt of malonic acid in place of the disilver salt of 1,1-cyclobutanedicarboxylic acid, giving 0.57 g of the desired product, mp 250°–255° C.

EXAMPLE 16

[3,4-Dihydroxy-3-cyclobutene-1,2-dionato(2-)-O$^3$,O$^4$](tetrahydro-4H-pyran-4,4-dimethanamine-N,N')platinum The procedure of Example 13 was repeated, using 0.66 g of the disilver salt of 3,4-dihydroxy-3-cyclobutene-1,2-dicarboxylic acid in place of the 1,1-cyclobutanedicarboxylic acid, giving 0.3 g of the desired product, mp 180°–185° C. (dec.).

EXAMPLE 17

(Tetrahydro-4H-pyran-4,4-dimethanamine-N,N')tetrachloroplatinum

A 1.8 g portion of dichloro(tetrahydro-4H-pyran-4,4-dimethanamine-N,N')platinum is suspended in 40 ml of 0.5N hydrochloric acid and heated to 100° C. A slow stream of chlorine gas is bubbled through the reaction mixture. Within a few minutes a clear solution is obtained. Bubbling of chlorine gas is continued for 2 hours. Nitrogen is bubbled through the reaction mixture to remove chlorine gas and the solution evaporated to dryness in vacuo. The yellow residue is taken up in 250 ml of methanol and the solution is filtered. The filtrate is evaporated to give 1.0 g of the desired product as a yellow solid.

EXAMPLE 18

[1,1-Cyclobutanedicarboxylato(2-)-0,0'](tetrahydro-4H-pyran-4,4-dimethanamine-N,N')dihydroxyplatinum A 1.2 g portion of [1,1-cyclobutanedicarboxylato(2-)-$O^1,O^1$](tetrahydro-4H-pyran-4,4-dimethanamine-N,N')platinum is suspended in 5 ml of distilled water. A 25 ml portion of 30% hydrogen peroxide is added. Stirring is carried out during 0.5 hour at room temperature, thereafter one hour under reflux. The suspension is cooled and the solid substance is filtered, washed with water and dried under reduced pressure, giving 0.4 g of the desired product.

EXAMPLE 19

[L-Threo-3-hexulosonato(2-)$C^2,O^5$-gamma-lactone](tetrahydro-4H-pyran-4,4-dimethanamine-N,N')platinum A solution of 1.36 g of silver nitrate in 10 ml of water was added to a suspension of 1.64 g of dichloro(tetrahydro-4H-pyran-4,4-dimethanamine-N,N')platinum in 100 ml of water and stirred in the dark for 4 hours followed by filtration. The filtrate was mixed with a solution of 1.58 g of L-ascorbic acid sodium salt in 10 ml of water and then filtered. The filtrate was stirred in the dark overnight and then refiltered. This filtrate was evaporated to dryness, the residue dissolved in 5 ml of water and added to 200 ml of ethanol. The resulting suspension was refrigerated for 2 hours and the solid collected, giving 1.07 g of the desired product.

EXAMPLE 20

Tetrahydro-4H-thiopyran-4,4-dimethanamine, 1,1-dioxide

A mixture of 38.2 g of bis(2-chloroethyl)sulfone, 13.2 g of malononitrile, 55.28 g of potassium carbonate and 800 ml of acetonitrile is refluxed on a steam bath for 24 hours, then filtered while hot. The filtrate is evaporated and the residue crystallized with charcoal treatment from 100 ml of ethanol, giving 10.6 g of tetrahydro-4H-thiopyran-4,4-dicarbonitrile, 1,1-dioxide as colorless crystals.

A 180 ml portion of 1N borane in tetrahydrofuran is added rapidly, but dropwise, to a solution of 11.05 g of tetrahydro-4H-thiopyran-4,4-dicarbonitrile, 1,1-dioxide in 150 ml of tetrahydrofuran. This mixture is warmed, then cooled to room temperature in an ice bath and then stirred for 64 hours at room temperature. A 100 ml portion of ethanol is added dropwise, then the mixture is stirred for 4 hours and then evaporated to dryness. The residue is taken up in 100 ml of water, acidified with 50 ml of 6N hydrochloric acid and extracted three times with ether. The remaining aqueous layer is evaporated to dryness. The residue is boiled in 300 ml of methanol and filtered while hot. The filtrate is treated with 200 ml of ether and cooled. The resulting solid is collected, washed with ether and dried, giving 9.1 g of the desired product.

EXAMPLE 21

Dichloro(tetrahydro-4H-thiopyran-4,4-dimethanamine-1,1-dioxide-N,N')platinum

A mixture of 2.65 g of tetrahydro-4H-thiopyran-4,4-dimethanamine, 1,1-dioxide and 1.64 g of sodium acetate in 50 ml of water is treated with 4.15 g of potassium tetrachloroplatinate. The reaction is repeatedly filtered to remove successive crops of black to red crystals. When no more precipitates formed, the mixture is allowed to stand overnight. The gold crystals are collected, giving 430 mg of the desired product.

EXAMPLE 22

[1,1-Cyclobutanedicarboxylato(2-)$O^1,O^1$](tetrahydro-4H-thiopyran-4,4-dimethanamine-1,1-dioxide-N,N')platinum A mixture of 916 mg of dichloro(tetrahydro-4H-thiopyran-4,4-dimenthanamine-N,N')platinum and 716 mg of the disilver salt of 1,1-cyclobutanedicarboxylic acid in 75 ml of water is stirred in the dark overnight, then filtered and washed with water. The combined filtrate and wash is evaporated to dryness, giving 820 mg of the desired product.

EXAMPLE 23

1-Methyl-4,4-piperidinedimethanamine, trihydrochloride

A mixture of 31.2 g of bis(chloroethyl)methylamine, 13.2 g of malonitrile, 55.28 g of potassium carbonate and 800 ml of acetonitrile is refluxed on a steam bath for 24 hours, then filtered while hot. The filtrate is evaporated and the residue crystallized with charcoal treatment from 100 ml of ethanol, giving 10.6 g of 1-methylpiperidine-4,4-dicarbonitrile, as colorless crystals.

A 180 ml portion of 1N borane in tetrahydrofuran is added rapidly, but dropwise, to a solution of 8.95 g of 1-methylpiperidine-4,4-dicarbonitrile, in 150 ml of tetrahydrofuran. This mixture is warmed, then cooled to room temperature in an ice bath and then stirred for 64 hours at room temperature. A 100 ml portion of ethanol is added dropwise, then the mixture is stirred for 4 hours and then evaporated to dryness. The residue is taken up in 100 ml of water, acidified with 50 ml of 6N hydrochloric acid and extracted three times with ether. The remaining aqueous layer is evaporated to dryness. The residue is boiled in 300 ml of methanol and filtered while hot. The filtrate is treated with 200 ml of ether and cooled. The resulting solid is collected, washed with ether and dried, giving 8.51 g of the desired product.

EXAMPLE 24

Dichloro(1-methylpiperidinedimethanamine-N,N')platinum

A mixture of 2.67 g of 1-methyl-4,4-piperidinedimethanamine, trihydrochloride and 2.46 g of sodium acetate in 50 ml of water is treated with 4.15 g of potassium tetrachloroplatinate. The reaction is repeatedly filtered to remove successive crops of black to red crystals. When no more precipitates formed, the mixture is allowed to stand overnight. The gold crystals are collected, giving 410 mg of the desired product.

EXAMPLE 25

[1,1-Cyclobutanedicarboxylato(2-)-$O^1,O^1$](1-methyl-piperidinedimethanamine-N,N')platinum A mixture of 850 mg of dichloro(1-methyl-piperidinedimethanamine-N,N') platinum and 716 mg of the disilver salt of 1,1-cyclobutanedicarboxylic acid in 75 ml of water is stirred in the dark overnight, then filtered and washed with water. The combined filtrate and wash is evaporated to dryness, giving 780 mg of the desired product.

EXAMPLE 26

1-Acetyl-4,4-piperidinedimethanamine, dihydrochloride

A mixture of 36.8 g of N,N-bis(chloroethyl) acetamide, 13.2 g of malononitrile, 55.28 g of potassium carbonate and 800 ml of acetonitrile is refluxed on a steam bath for 24 hours, then filtered while hot. The filtrate is evaporated and the residue crystallized with charcaol treatment from 100 ml of ethanol, giving 10.7 g of 1-acetyl-4,4-piperidine-4,4-dicarbonitrile, as colorless crystals.

A 180 ml portion of 1N borane in tetrahydrofuran is added rapidly, but dropwise, to a soluton of 10.6 g of 1-acetyl-4,4-piperidine-4,4-dicarbonitrile, in 150 ml of tetrahydrofuran. This mixture is warmed, then cooled to room temperature in an ice bath and then stirred for 64 hours at room temperature. A 100 ml portion of ethanol is added dropwise, then the mixture is stirred for 4 hours and then evaporated to dryness. The residue is taken up in 100 ml of water, acidified with 50 ml of 6N hydrochloric acid and extracted three times with ether. The remaining aqueous layer is evaporated to dryness. The residue is boiled in 300 ml of methanol and filtered while hot. The filtrate is treated with 200 ml of ether and cooled. The resulting solid is collected, washed with ether and dried, giving 9.1 g of the desired product.

EXAMPLE 27

Dichloro(1-acetyl-4,4-piperidinedimethanamine-N,N')platinum

A mixture of 2.58 g of 1-acetyl-4,4-piperidinedimethanamine, dihydrochloride and 1.64 g of sodium acetate in 50 ml of water is treated with 4.15 g of potassium tetrachloroplatinate. The reaction is repeatedly filtered to remove successive crops of black to red crystals. When no more precipitates formed, the mixture is allowed to stand overnight. The gold crystals are collected, giving 420 mg of the desired product.

EXAMPLE 28

[1,1-Cyclobutanedicarboxylato(2-)-$O^1,O^1$](1-acetyl-4,4-piperidinedimethanamine-N,N')platinum A mixture of 906 mg of dichloro(1-acetyl-4,4-piperidinedimethanamine-N,N')platinum and 716 mg of the disilver salt of 1,1-cyclobutanedicarboxylic acid in 75 ml of water is stirred in the dark overnight, then filtered and washed with water. The combined filtrate and wash is evaporated to dryness, giving 750 mg of the desired product.

What is claimed is:

1. A compound selected from those of the formulae:

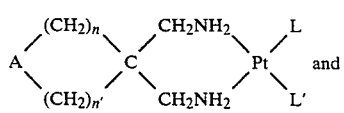

and

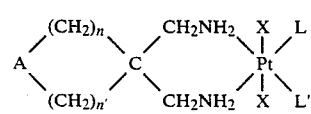

where A is O, n and n' are the same and are 2,; L and L' are selected from the group consisting of halide, nitrate, sulfate, and a monobasic carboxylate selected from the group consisting of acetate, hydroxy acetate and propionate; or L and L' may be a diabsic carboxylate selected from the group consisting of

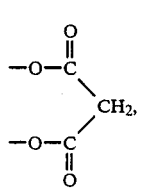

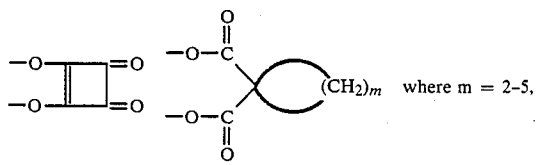 where m = 2-5,

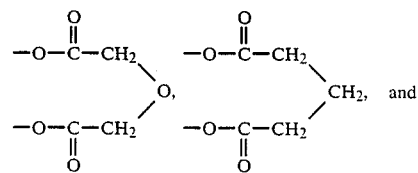

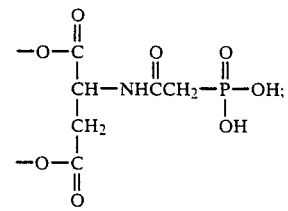

or L and L' taken together may be a tribasic carboxylate seleced from the group consisting of

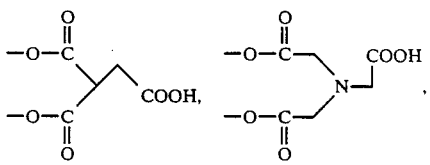

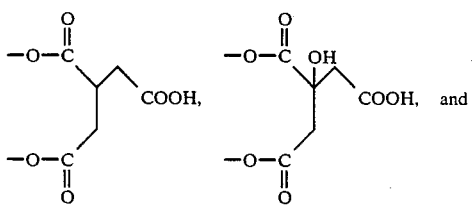

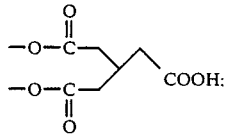

or L or L' taken together is ascorbic acid and X is selected from the group consisting of halogen and hydroxy.

2. The compound according to claim 1, [3,4-dihydroxy-3-cyclobutene-1,2-dionato(2-)-$O^3,O^4$](tetrahydro-4H-pyran-4,4-dimethanamine-N,N')platinum.

3. The compound dichloro-(tetrahydro-4H-pyran-4,4-dimethanamine-N,N)platinum.

4. The compound [1,1-cyclobutanedicarboxylato(2-)-$O^1,O^1$](tetrahydro-4H-pyran-4,4-dimethanamine-N,N')platinum.

5. The compound [[2,2'-oxybis[acetato]](2-)-$O^1, O^1$]tetrahydro-4H-pyran-4,4-dimethanamineN,N') tetra- chloro platinum.

6. The compound [propane dionato (2-)-$O^1,O^3$](tetrahydro-4H-pyran-4,4-dimethanamine-N,N')platinum.

7. The compound tetrahydro-4H-pyran-4,4-dimethanamine-N,N') tetrachloroplatinum.

8. The compound [1,1-cyclobutanedicarboxylato (2-)-$O^1$, $O^1$](tetrahydro-4H-pyran-4,4-dimethanamine-N,N') dihydroxyplatinum.

9. The compound [3,4-dihydroxy-3-cyclobutene-1,2-dionato(2-)-$O^3,O^4$](tetrahydro-4H-pyran-4,4-dimethanamine-N,N') platinum.

10. A composition of matter in dosage unit form for administering by intravenous, intramuscular, subcutaneous, parenteral or intraperitoneal routes comprising an amount of from about 1 mg to about 1.2 g per square meter of mammalian body surface area of a compound of claim 1 in association with a pharmaceutically acceptable carrier.

11. A composition of matter, in dosage unit form for administering by intravenous, intramuscular, subcutaneous, parenteral or intraperitoneal routes, which consists essentially of an amount of fromm about 1 mg to about 1.2 g per square meter of mammalian body surface area of a compound of claim 1 in association with a pharmaceutically acceptable carrier.

12. A composition of matter, in dosage unit form for administering by intravenous, intramuscular, subcutaneous, parenteral or intraperitoneal routes, which consists of an amount of from about 1 mg to about 1.2 g per square meter of mammalian body surface area of a compound of claim 1 in association with a pharmaceutically acceptable carrier.

13. A composition of matter on dosage unit form for administering by intravenous, intramuscular, subcutaneous, parenteral or intraperitoneal routes which comprises an amount of from about 1 mg to about 1.2 g per square meter of mammalian body surface area of a compound of claim 4 association with a pharmaceutically acceptable carrier.

14. A composition of matter in dosage unit form for administering by intravenous, intramuscular, subcutaneous, parenteral or intraperitoneal routes which comprises an amount of from about 1 mg to about 1.2 g per square meter of mammalian body surface area of a compound of claim 5 association with a pharmaceutically acceptable carrier.

15. A composition of matter in dosage unit form for administering by intravenous, intramuscular, subcutaneous, parenteral or intraperitoneal routes which comprises an amount of from about 1 mg to about 1.2 g per square meter of mammalian body surface area of a compound of claim 6 association with a pharmaceutically acceptable carrier.

16. A composition of matter in dosage unit form for administering by intravenous, intramuscular, subcutaneous, or parenteral or intraperitoneal routes which comprises an amount of from about 1 mg to about 1.2 g per square meter of mammalian body surface area of a compound of claim 7 association with a pharmaceutically acceptable carrier.

17. A composition of matter in dosage unit form for administering by intravenous, intramuscular, subcutaneous, parenteral or intraperitoneal routes which comprises an amount of from about 1 mg to about 1.2 g per square meter of mammalian body surface area of a compound of claim 8 association with a pharmaceutically acceptable carrier.

18. A method of treating melanocarcinomas, lung carcinomas and mammary tumors in warm-blooded animals which comprises administering an effective, oncolytic amount of a compound of claim 1.

19. A method of treating melanocarcinomas, lung carcinoma and mammary tumors in warm-blooded animals which comprises administering an affective oncolytic amount of a compound of claims 4, 5, 6, 7 or 8.

* * * * *